United States Patent [19]

Yoon

[11] 4,433,680

[45] Feb. 28, 1984

[54] POLYURETHANE CASTING MATERIAL

[75] Inventor: Hee K. Yoon, North Brunswick, N.J.

[73] Assignee: Johnson & Johnson Products, Inc., New Brunswick, N.J.

[21] Appl. No.: 347,596

[22] Filed: Feb. 10, 1982

[51] Int. Cl.³ .............................................. A61F 5/04
[52] U.S. Cl. ..................................................... 128/90
[58] Field of Search ............... 128/90, 89 R; 526/915; 521/115, 170, 125, 126, 127, 128; 544/47, 74; 528/53

[56] References Cited

U.S. PATENT DOCUMENTS 3,645,925 2/1972 Speranza et al. .................. 521/115
4,344,423 8/1982 Evans et al. ........................ 128/90

FOREIGN PATENT DOCUMENTS 2357931 5/1975 Fed. Rep. of Germany .
2651089 11/1980 Fed. Rep. of Germany .
1578895 11/1980 United Kingdom .
WO81/00671 of 1981 PCT Int'l Appl. .

*Primary Examiner*—C. Fred Rosenbaum
*Assistant Examiner*—T. J. Wallen
*Attorney, Agent, or Firm*—Michael Q. Tatlow

[57] ABSTRACT

An improved polyurethane orthopaedic cast bandage is disclosed. The bandage is a polyurethane prepolymer coated on an open-weave, fibrous substrate. The prepolymer contains dimorpholinodiethylether as a catalyst which gives the cast bandage increased shelf stability and excellent set time.

6 Claims, No Drawings

POLYURETHANE CASTING MATERIAL

FIELD OF THE INVENTION

The present invention relates to an improved polyurethane orthopaedic casting bandage which is used to form orthopaedic casts.

BACKGROUND OF THE INVENTION

Plaster of Paris casts have been used to immobilize body members for some time. These bandages are made by depositing plaster of Paris on a reinforcing scrim material such as gauze. When the plaster of Paris is dipped in water, the alphahemihydrate of calcium sulfate is converted to calcium sulfate dihydrate, which results in the hardening of the cast. Plaster of Paris casts, however, suffer from a number of disadvantages. X-ray transmission through the cast to determine whether a fracture has been properly set is extremely difficult. In addition, the cast is quite heavy and restricts the mobility of the patient wearing the cast. The casts are also very sensitive to water and may seriously lose their load-bearing capability if they become wet. In addition, the air permeability of the plaster of Paris cast is very limited, and, as a result, they do not allow evaporation of moisture from the skin beneath the cast, which may result in skin irritation beneath the cast.

In order to overcome the disadvantages of plaster of Paris casts, numerous attempts have been made to develop plastic or plastic-reinforced materials as a replacement for plaster of Paris.

U.S. Pat. Nos. 3,241,501 and 3,881,473 disclose casts which are made with a flexible fabric impregnated with a polymer which is capable of being cured by ultraviolet light. Although this casting material overcomes some of the disadvantages of plaster of Paris cast material, it requires a different technique in its application and also requires the use of an ultraviolet light source in order to cure the cast. These casts also require significantly longer times for the cast to set before they will be load bearing.

More recent attempts to produce substitutes for plaster of Paris include the polyurethane polymers disclosed in German Offenlegenschrift Nos. 2353212 and 2357931, U.K. Pat. No. 1,578,895, and PCT Application No. W081/00671. These bandages are open-weave fabrics coated with polyurethane prepolymers, that is, reaction products of isocyanates and polyols. The bandages are dipped into water in the same manner as the plaster of Paris and then applied to the limb of a patient. The water causes the prepolymer to polymerize and form a rigid polymer structure. In order to obtain the desired rapid hardening or setting of the bandage, it is necessary to have a catalyst system incorporated in the prepolymer formulation. The casting material disclosed in U.K. Pat. No. 1,578,895 employs amino polyols as catalysts and as the polyol components. The casting material disclosed in W081/00671 employs dimethylethanolamine (DMEA) or a mixture of DMEA and bis(2-dimethylaminoethyl) ether. These catalyst systems provide acceptable hardening of the prepolymers by catalyzing the water-isocyanate reaction. However, the presence of these catalysts in the prepolymer system also causes side reactions which gel the prepolymer in the bandage package. These side reactions are generally branching reactions resulting in biuret and allophanate formation and some formation of isocyanate trimer. The gelatin caused by the side reactions causes premature hardening or setting of the bandage in the package and, therefore, poor shelf life or shelf stability. The lack of adequate shelf stability can cause numerous difficulties in attempting to form a cast from such cast bandages. In order for the bandages to have an acceptable set time, it is necessary to adjust the polyurethane prepolymer components to the extent that the reaction with water is such that the set time of the finished bandage is satisfactory. The set time is the time after the bandage is dipped in water to the point where the cast made from the bandage is rigid and the limb of the patient is immobilized. In order to obtain acceptable set times, the polyurethane prepolymer bandages of prior art products had a limited shelf life, i.e., less than 12 months, which is not practical commercially.

Although there are numerous catalysts available to catalyze the water-isocyanate reaction of the prepolymer, these catalysts are not necessarily suitable for use in a cast bandage, as these catalysts do not provide adequate shelf life for the cast bandage. The particular catalyst employed in the present invention has previously been employed in the formation of polyurethane foams (see U.S. Pat. No. 3,645,925) and reaction injection molding elastomers (see U.S. Pat. No. 4,273,885).

SUMMARY OF THE INVENTION

The present invention relates to a polyurethane cast material which comprises a fibrous substrate coated with a polyurethane prepolymer which contains a dimorpholinodiethylether catalyst. The use of dimorpholinodiethylether as a catalyst avoids the problems of storage stability common with other catalyst systems. The cast material is very stable, having an extremely long shelf life, and yet it will set after being applied to the patient within 10 minutes. The dimorpholinodiethylether catalyst used in the present invention catalyzes the formation of the side reactions at a much lower rate than the catalyst previously used.

DETAILED DESCRIPTION OF THE INVENTION

Isocyanates

The aromatic isocyanates useful in the prepolymer system of the present invention may be any of the aromatic polyisocyanates known in polyurethane chemistry which are described, for example, in "Polyurethanes, Chemistry and Technology," Part I, Interscience Publishers (1962).

The aromatic polyisocyanates preferred include tolylene diisocyanate (TDI), such as the 80/20 or the 65/35 isomer mixture of the 2,4 and 2,6 isomeric forms; diphenylmethane diisocyanate (MDI), such as the 4,4', the 2,4' and the 2,2' isomeric forms or isomeric mixtures thereof; modified MDI containing additional functional groups such as carbodiimide groups, urethane groups and allophanate groups and polymethylene polyphenylisocyanates (Polymeric MDI) which are derived from phosgenation of the condensation products of aniline and formaldehyde. Most preferred polyisocyanate is the carbodiimide containing MDI which is readily available commercially, e.g., Isonate®143L and Rubinate®XI-168.

Polyols

The polyols useful in the prepolymer system of the present invention include polyether polyols and polyester polyols. The polyether polyols may be prepared by the polymerization of epoxides, such as ethylene oxide, propylene oxide, butylene oxide, tetrahydrofuran, styrene oxide, or mixtures thereof in the presence of the catalysts. The polyester polyols include the reaction products of polyhydric alcohols and polybasic carboxylic acids. Instead of free carboxylic acids, the corresponding polycarboxylic acid anhydrides or the corresponding polycarboxylic acid esters of low alcohols or mixtures thereof may be used for preparing the polyesters. Polyesters of lactones, such as ε-caprolactone may also be used.

Most preferred polyols are the poly(oxypropylene) diols and triols, having a molecular weight of from 400 to 2,000. Examples of polyols are Pluracol ®P1010 and Poly G ®36-232.

The preferred polyurethane prepolymer is made from diphenylmethanediisocyanate containing carbodiimide groups. These diisocyanates are reacted with a polyol containing two to three functional groups. The polyols may be diols or triols or mixtures of diols and triols. The preferred polyols are poly(oxypropylene)glycol having a hydroxyl number of 105 and poly(oxypropylene) triol having a hydroxyl number of 232. The molecular weight of the polyols is usually below 2,000, preferably in the range of 700 to 1,500, and most preferably between 700 and 1,100.

The ratio of the polyisocyanate to the polyol in the prepolymer reaction mixture is best expressed by the equivalent ratio. Equivalent weight is determined by dividing the molecular weight of each particular component by its functionality or number of functional groups in the compound. The equivalent ratio is the ratio of the equivalency of the isocyanate to the polyol. The equivalent ratio in the present system should be between 2:1 to approximately 15:1 equivalents of the polyisocyanate to the polyol and preferably from 2:1 to 10:1. These components are combined so that there is an excess of from 5% to 30% NCO groups in the prepolymer. The prepolymer also contains from 0.1% to 10% by weight based on the weight of the total mixture of the dimorpholinodiethylether catalyst having the following structure:

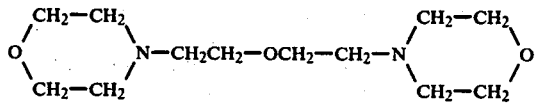

The preferredd amount of catalyst is from 1% to 4% based on the weight of total mixture. Above 5% by weight of catalyst, the shelf life of the cast bandage begins to be reduced.

It is also possible to use a small amount of a co-catalyst with the dimorpholinodiethylether catalyst. Such co-catalyst may be a commonly used urethane catalyst such as a tertiary amine or a metal catalyst.

In addition to the polyisocyanate, the polyol and the catalyst, the prepolymer reactants may also include a small amount, 0.01% to 1% by weight, of a stabilizer such as benzoyl chloride and a surfactant agent such as a silicone liquid used as an antifoam agent. The surfactant or antifoam agent would be present in an amount of from 0.01% to 1% by weight.

The prepolymer is reacted under the following conditions:

A reaction vessel is placed under a vacuum, and the isocyanate component is added to the vessel. The vacuum is released, nitrogen is added to the vessel, and the antifoam agent is added to the isocyanate component. Benzoyl chloride is added to the vessel and mixed thoroughly with the reactants. Vacuum dried polyols containing the catalyst are then added to the reaction vessel over a period of from 20 to 25 minutes. The reaction temperature is maintained between 50° C. and 60° C. for one hour. The completion of the reaction can be determined by obtaining a sample of the reaction product and testing for the desired level of NCO in the prepolymer.

The prepolymer is then applied in a dry atmosphere to a substrate by reverse roll coating or other coating technique to form the cast bandage. The substrate may be a knitted or woven fabric having a weight of from 50 to 350 grams per square meter and preferably between 70 and 290 grams per square meter. The fibers in the fabric may be synthetic fibers such as polyester, or natural fibers such as cotton or may be fiberglass. Suitable fabrics for the substrate include those disclosed in U.S. Pat. Nos. 3,882,857; 3,787,272 and 4,134,397. The weight of prepolymer on the fabric is from about 85 to 200 grams per square meter, preferably between 100–150 grams per square meter. Immediately after the prepolymer is applied to the fabric, the coated fabric is packaged in an inert atmosphere to prevent any contact with atmospheric moisture.

When the bandage is to be used, it is removed from the package and placed in water for from 3 seconds to 30 seconds, but preferably between 5 and 10 seconds. It is removed from the water and applied to the patient, usually over a tubular, knitted fabric and a cast padding. The bandage will set within less than 10 minutes to a condition where it is capable of immobilizing the fracture.

In the following Examples, the "Gel Time" of the polymer was determined by placing 25 ml. of the prepolymer in a 50 ml. tube. The tube is placed in an oven at 70° C. The tubes are removed from the oven at designated times, and the surface of the prepolymer in the tube is probed with a glass rod. The Gel Time is the time when the surface of the prepolymer is hard and the rod will not enter or move the prepolymer. The Gel Time has been found to be an excellent accelerated aging test useful in predicting the shelf stability of the cast bandages when the bandages are stored at room temperature. Generally, a Gel Time of 10 days at 70° C. would indicate shelf stability of approximately 9 months at 23° C. For example, a Gel Time of 30 days would indicate a shelf stability in excess of 24 months at 23° C.

The set time or setting time of the cast in a laboratory is determined by dipping the cast bandage in water at 75° F. and squeezing the bandage four or five times under the surface of the water. A test cylinder is formed by wrapping a layer of the bandage on a 2¾ inch wooden dowel. The test cylinder is immediately removed from the dowel. The set time is determined by attempting to indent the test cylinder by fingernail pressure. When the bandage or test cylinder cannot be indented, the set time is recorded.

EXAMPLE I

A series of prepolymers were prepared with the catalysts indicated in Table I. Each of the prepolymers were prepared from a diphenylmethanediisocyanate containing carbodiimide groups and mixed polyols. The mixed polyols were polyether polyols comprised of 60% by weight of a diol having a molecular weight of approximately 1010 and 40% by weight of a triol having a molecular weight of approximately 730. The prepolymer also contained 0.05% benzyol chloride and 0.075% of a silicone surfactant. The diisocyanate and the polyols were reacted in a ratio of 4 to 1, at a temperature of 50°-60° C. The Gel Time of the prepolymer and the set time of a cast made with the prepolymer coated on a polyester/cotton substrate are shown in Table I.

TABLE I

| Catalyst | Catalyst Conc. | Gel Time | Set Time (Min.) |
|---|---|---|---|
| 1. bis(2-dimethylaminoethyl) ether | 0.3 | 11 | 5.0 |
| 2. triethylenediamine (DABCO) | 0.3 | 5 | 6.2 |
| 3. cyclohexylamine (Polycat 9) | 0.4 | 4 | 10+ |
| 4. cyclohexylamine (Polycat 70) | 0.4 | 6 | 9.0 |
| 5. cyclohexylamine (Polycat 77) | 0.5 | 3 | 10+ |
| 6. dimethylethanolamine | 1.0 | 1 | 4.0 |
| 7. substituted morpholine | 1.0 | 2 | 6.5 |
| 8. dimethylpiperazine | 0.3 | 16 | 14+ |
| 9. dimethylaminoethyl-3-dimethyl aminopropylether | 1.0 | 4 | 15+ |
| 10. dimorpholinoethane | 2.0 | 21 | 15+ |
| 11. tetraethylethyleneamine | 0.3 | 3 | slow |
| 12. DABCO & dimethylethanolamine | 0.3 | 5 | slow |
| 13. imidazole | 2.0 | 11 | 15+ |
| 14. triethanolamine | 0.3 | 8 | no set |
| 15. 1,3 bis(dimethylamino) 2-propanol | 0.3 | 7 | very slow |
| 16. dimethylaminoethoxyethanol | 1.0 | 3 | 4.7 |
| 17. dimorpholinodiethylether | 1.0 | 34+ | 6.0 |
| 18. dimorpholinodiethylether | 2.0 | 31 | 4.5 |
| 19. dimorpholinodiethylether | 3.0 | 28 | 4.0 |

It is evident from the results shown in Table I that the dimorpholinodiethylether catalyst provides the long Gel Times and the short set times that are desirable and required for a polyurethane cast bandage.

EXAMPLE II

To a 5 liter resin flask equipped with a thermometer, a stirrer, a nitrogen inlet and a drying tube, 3007 grams of Isonate ®143L (modified diphenylmethane diisocyanate) was charged. Then, 3.62 grams of Dow Corning DC-200 (30,000 cs.) and 2.41 grams of benzoyl chloride were added. The charge was stirred for 15 minutes to mix thoroughly. To this, 1828 grams of Pluracol ®P1010 (60% by weight) and Poly G ®36-232 (40% by weight), to which was added 85 grams of dimorpholinodiethylether, was added while stirring. The polyols were dried prior to mixing with the catalyst. The equivalent ratio of NCO to OH was 4.18:1. The addition of the polyols was made through a dropping funnel in 20-25 minutes. After the addition was completed, the polymerization was carried out at 50°-60° C. for one hour. The NCO content of the prepolymer obtained was about 13.9%. The Gel Time of the prepolymer at 70° C. was 33 days. The set time of the bandage made with this prepolymer on polyester/cotton fabric was about 4.7 minutes.

EXAMPLE III

To a 1 liter reaction kettle equipped with a thermometer, a stirrer, a nitrogen inlet and a drying tube, 665 grams of Papi ®27 (polymeric diphenylmethanediisocyanate) was charged. Then, 0.76 grams of Dow Corning DC-200 (30,000 cs.) and 0.51 grams of benzoyl chloride were added. The charge was stirred for 15 minutes to mix thoroughly. To this, 347 grams of the blend of the 208 grams of Pluracol ®P1010, 139 grams of Pluracol ®GP 730 and 17.7 grams of dimorpholinodiethylether was added while stirring. The polyols were dried prior to mixing with the catalyst. The equivalent ratio of NCO to OH was 5.0:1.0. After the addition of the blend, the polymerization was carried out at 50°-60° C. for one hour. The NCO content of the prepolymer obtained was 15.12%. The Gel Time of the prepolymer at 70° C. was about 35 days. The set time of the bandage made with this prepolymer on polyester/cotton fabric was about 4.8 minutes.

EXAMPLE IV

To a 1 liter reaction kettle equipped with a thermometer, a stirrer, a nitrogen inlet and a drying tube, 522 grams of molten Isonate ®125M (pure diphenylmethanediisocyanate) was charged. Then, 0.65 grams of Dow Corning DC-200 (30,000 cs.) and 0.44 grams of benzoyl chloride were added. The charge was stirred for 15 minutes to mix thoroughly. To this, 347 grams of the blend of 208 grams of Pluracol ®P1010, 139 grams of Poly G ®36-232 and 15.2 grams of dimorpholinodiethylether were added while stirring. The polyols were dried prior to mixing with the catalyst. The equivalent ratio of NCO to OH was 4.17:1. After the addition of the blend, the polymerization was carried out at 50°-60° C. for one hour. The NCO content of the prepolymer obtained was 14.42%. The prepolymer gelled in 32 days at 70° C. The set time of the bandage made with this prepolymer on polyester/cotton fabric was about 5.0 minutes.

I claim:

1. A storage-stable orthopaedic cast bandage comprising a water-activatable polyurethane prepolymer coated on an open-weave fibrous substrate, said prepolymer comprising an aromatic polyisocyanate and a polyol in an equivalent ratio of from 2:1 to 15:1 and containing from 0.1% to 10%, based on the weight of prepolymer, of dimorpholinodiethylether as a catalyst.

2. The cast bandage of claim 1 in which the aromatic polyisocyanate is a diphenylmethane diisocyanate containing carbodiimide groups.

3. The cast bandage of claim 1 in which the polyol is a mixture of poly(oxypropylene) diols and triols having a molecular weight of from 400 to 2,000.

4. The cast bandage of claim 1 containing from 1% to 4% by weight of dimorpholinodiethylether.

5. The cast bandage of claim 1 in which the prepolymer contains 0.01% to 1% by weight of benzoyl chloride and 0.01% to 1% by weight of an antifoam agent.

6. The cast bandage of claim 1 in which the percent NCO in the prepolymer is from 5% to 30% by weight.

* * * * *